United States Patent [19] [11] 4,087,332
Hansen [45] May 2, 1978

[54] INDICATOR FOR USE IN SELECTION OF BACTERICIDAL AND BACTERISTATIC DRUGS AND METHOD FOR PRODUCING SAME

[76] Inventor: Kai Aage Hansen, Villavej 13, 9240 Nibe, Denmark

[21] Appl. No.: 818,075

[22] Filed: Jul. 22, 1977

Related U.S. Application Data

[63] Continuation-in-part of Ser. No. 684,240, May 7, 1976, abandoned.

[51] Int. Cl.$^2$ .................................................. C12K 1/00
[52] U.S. Cl. .............................. 195/127; 195/103.5 K; 23/253 TP
[58] Field of Search ......................... 195/103.5 K, 127; 23/253 TP

[56] References Cited
U.S. PATENT DOCUMENTS

| | | | |
|---|---|---|---|
| 2,904,474 | 9/1959 | Forg | 195/103.5 M |
| 3,127,281 | 3/1974 | Meyer | 195/103.5 R |
| 3,509,026 | 4/1970 | Sanders | 195/103.5 M |
| 3,846,247 | 11/1974 | Kronish et al. | 195/103.5 M |

Primary Examiner—Alvin E. Tanenholtz
Attorney, Agent, or Firm—Edward F. Levy

[57] ABSTRACT

A test strip is provided for visually indicating the effectiveness of selected antibiotics, bactericidal drugs, or the like in combatting microorganisms in specimens taken from a patient. The test strip comprises a porous, water absorbent or adsorbent body which may be made of plastic foam material, upon the porous surface of which spaced stripes of testing material are applied by automatic printing or coating apparatus. One of the stripes contains a nutrient substrate for the tested microorganisms and the other stripes contain a mixture of the same nutrient substrate and various selected bactericidal and bacteristatic drugs. The test strip is initially manufactured as a strip of long length with the stripes extending longitudinally thereon, and is then separated into short transverse panels for use in the testing. Moisture barriers are formed between the stripes by the application of pressure or heat to the porous surface of the test strip.

12 Claims, 3 Drawing Figures

INDICATOR FOR USE IN SELECTION OF BACTERICIDAL AND BACTERISTATIC DRUGS AND METHOD FOR PRODUCING SAME

This application is a continuation-in-part of my copending U.S. Patent Application Ser. No. 684,240 filed May 7, 1976 now abandoned and entitled "INDICATOR FOR USE IN SELECTION OF BACTERICIDAL AND BACTERISTATIC DRUGS AND METHOD FOR PRODUCING SAME".

The present invention relates to apparatus, in the form of portable strips, for indicating the effectiveness of various antibiotics in treating selected microorganisms being tested, and thus permitting selection of the most effective antibiotics. The invention also relates to a novel method of producing such strips with a reliability in the manufacturing method heretofore unobtainable, and yet at an economical cost.

In the selection of bactericidal and bacteristatic drugs by a physician or veterinary for treatment of infectious diseases, both speed and safety is often of decisive importance, while reasonable cost of the test equipment is also an important consideration. In other words, there is a need for means which enables a physician to make such a selection quickly and easily, and in a faultless manner. For this purpose it is not satisfactory to send disease samples or specimens to a distant laboratory for cultivation by the usual methods. Aside from the time involved, it is often difficult, if not impossible to collect and deliver to the laboratory a sample which is not contaminated by irrelevant bacteria or fungi, even if the laboratory is nearby or in the same premises.

It is known to provide glass or plastic vessels which are subdivided into a plurality of partitions within each of which is cast a characteristic nutrient substrate, which, upon cultivation by body temperature, may provide guidance as to the types of bacteria which will breed in the particular substrate.

In U.S. Pat. No. 3,509,026 there is disclosed a liquid impermeable mounting strip to which are fastened a number of water-absorbent discs, for example discs fabricated of open-celled polyurethane foam. Each of the discs is saturated with a mixture of a nutrient substrate and a bactericidal or bacteristatic drug, with succeeding discs having a different content of drug either with respect to concentration or to type of drug. The aforementioned mounting strip, which supports impregnated discs of the type described, is secured to a somewhat wider strip in such a manner that the wider strip and the discs are placed on opposite surfaces of the mounting strip. The wider strip is perforated along its edges for automatically transporting the discs at a predetermined speed through an apparatus which not only serves as a growth chamber, but also is equipped for photometric measurement of the degree of cultivation.

In U.S. Pat. No. 3,846,247, there is described a diagnostic strip made of a highly absorbent or bibulous paper in which reagents are applied in selected areas by rollers, and moisture barriers are formed between these areas by applying successive layers of a specific liquid formulation to the paper strip by rollers. In this process, however, a suspension of unknown bacteria in saliva is separately incubated and subsequently applied to the paper strip, whereupon a color change in the impregnated reagent serves to identify the bacteria. Further, in accordance with the present invention, the test strip provided is made of a material which is sensitive to heat and/or pressure in such a manner that in the manufacture of the strips, the application of heat and/or pressure thereto will itself form sealed moisture barriers to prevent migration between test zones, without the necessity of adding any separate moisture sealing materials.

In U.S. Pat. No. 2,904,474 there is disclosed a bacteriological test strip of absorbent and swellable paper coated with a nutrient medium and a dye indicator. When a specimen is applied to the surface of the strip, the growth of bacteria colonies are shown by discoloration of the dye indicator and the presence of the bacteria can be determined quantitatively by the number of colored dots appearing on the strip.

U.S. Pat. No. 3,127,281 shows a strip of bibulous material impregnated by rollers with two or more different test reagents separated by liquid-impermeable barrier lines. The strip is dipped into a liquid to be tested, and the impregnated reagents change color by chemical reaction to indicate the presence of substances in the liquid being tested. No bacteriological growth is produced.

A drawback of conventional indicator means of the aforementioned types is that the fabrication and use thereof is not particularly simple. In addition, the apparatus requires more space than is desirable, and where the apparatus operates by providing photometric measurement of the microorganism growth, not only is a rather complicated technique required, but the physician must resort to a subjective estimate of the type of bactericidal or bacteristatic drug which, according to the result of cultivation, would be most effective for combatting the seeded microbes or fungi. This difficulty results from the fact that the growth of the seeded microorganisms is not observed directly, but only indirectly through reagents which change color or fluoresce as a result of chemical action of the cultivation process.

It is an object of the present invention to provide an indicator to be used for selection of bactericidal or bacteristatic drugs, the effectiveness of which drugs, for the treatment of a particular patient, is determined solely by direct inspection of the degree and nature of growth of seeded bacterial colonies.

Another object of the invention is the provision of a method for the fabrication of an indicator of the type described in an economical manner and yet with the indicator being capable of rapid and reliable use by a physician during the course of his ordinary daily practice without requiring any special laboratory equipment.

A further object of the invention is the provision of an indicator of the character described which may be manufactured economically by mass production techniques in which a number of bactericidal and bacteristatic drugs mixed with a nutrition substrate are applied in spaced areas to a surface of an elongated carrier by conventioned printing methods, and migration barriers are provided between these spaced areas during the manufacture of the indicator by the application of heated or pressure rollers to the surface of the carrier.

In accordance with the invention there is provided an indicator for use in the selection of bactericidal and bacteristatic drugs, which indicator comprises a solid elongated carrier sheet having an upper layer with a porour front surface and a moisture-tight backing. The upper layer has interconnected passages which are pervious to moisture and have a material consistency adapted to having its passages closed solely by application of heat or pressure thereto. A plurality of testing coatings are arranged on the front surface of said carrier in the form of spaced stripes extending parallel to the longitudinal axis of said carrier sheet. One of said coating stripes consists only of a nutrition substrate for bacteria and constitutes a comparison stripe. The other coating stripes constitute a mixture of a nutrition substrate and a different bactericidal or bacteristatic drug. The carrier sheet comprises a continuous length of adsorbent or absorbent sheet material with the porous front surface thereof serving as an integral mechanical carrier for the testing coatings.

A moisture barrier band is provided between each adjacent pair of coating stripes by the application of heat or pressure to the front surface of the carrier sheet and without application of any additional moisture-sealing material.

The carrier sheet is adapted to be separated transversely at even intervals into small transverse panels, each containing said coating strips, and in a preferred embodiment the carrier sheet is provided with evenly-spaced separation lines extending transversely thereof and perpendicular to the coating stripes for such separation into individual panels. The coating stripe sections on said panels, when impregnated by a testing specimen, serve as individual bacteria culture media, whereby differences in bacteria colonization between the comparison stripe and the other coating stripes may be ascertained by direct visual observation.

The aforementioned indicator is used by a physician in order to determine which particular drug on the carrier is most effective in treating the particular strain of microorganism with which the patient being testing is infected. The physician obtains a sample of phlegm or other liquid specimen containing the microorganism from the patient, and with a swab or the like applies a smear of the infected sample across the indicator strip, in such a manner to insure that the smear contacts all of the stripes containing the bactericidal and basteristatic drugs as well as the neutral, comparison nutrition substrate. After such seeding of the disease microorganism, the physician may directly observe the degree of growth of the seeded colonies on each stripe, and by the absence of growth at particular stripes, can determine which of the drugs is most effective in destroying the particular microorganism.

Additional objects and advantages of the invention will become apparent during the course of the following specification when taken in connection with the accompanying drawings in which.

Figure 1:
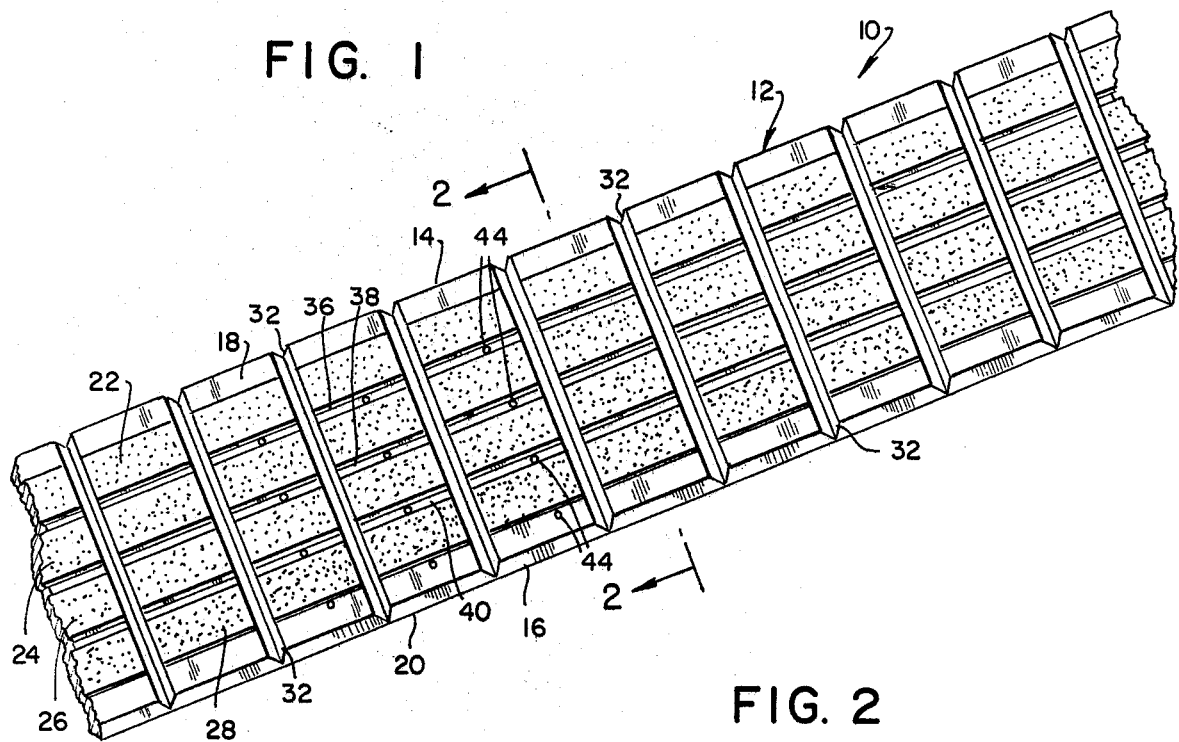
FIG. 1 is a top plan view of an indicator strip made in accordance with the present invention.

Referring in detail to the drawings, there is shown an indicator 10 which in its preferred form comprises an elongated body 12 of porous material. The body 12 has parallel longitudinal edges 14 and 16, an upper surface 18 and a lower surface 20. The upper surface 18 is capable of absorbing water, while the lower surface 20 is liquid impermeable. Applied directly on the upper surface 18 of the indicator body 12 are a plurality of spaced longitudinally-extending stripes 22, 24, 26 and 28, each of which contains a nutrition substrate, and all but one of which contains a selected bactericidal or bacteristatic drug mixed with the substrate. Moisture barriers are provided between said stripes, in a manner to be presently described, to prevent migration of liquid therebetween.

The indicator body 12 may be advantageously made of a plastic foam which is thermoplastic and/or pressure sensitive and which has the advantage of providing a very strong carrier which may be packaged in a sterile package which may be opened for removal of the indicator without damage immediately before the testing steps of infection and incubation of a specimen on the stripes 22, 24, 26 and 28. As one example, polyurethane foam is particularly suitable for fabrication of the indicator body 12, since this type of plastic foam may be easily processed by well-known methods, such as by cutting with a razor or sharp knife, to provide open cells on at least parts of the upper surface 18 and closed cells on the lower surface 20, so that the upper surface and upper layer of the indicator body are porous and water absorbent and the lower surface is impervious to water. The lower surface may be made water impervious by casting it or extruding it against a polished surface. As an alternative, the lower surface 20 may be covered by a thin polyurethane membrane which is not cellular, to render the lower surface water-proof. The use of polyurethane foam is also advantageous in that open-celled polyurethane foam has especially good absorbing properties, can withstand widely varying temperatures ranging from deep-freezing temperatures to temperatures of sterilization, and further provides an indicator body of very light weight which is economical in manufacture.

The indicator body 12 may also be made of other suitable foam plastic materials or of a paper material such as filter paper which is high absorbent. In this instance, the pulp of the paper is impregnated at the paper mill with, for example, a homogenously-dispersed plastic resin, to permit sealed moisture barrier lines to be applied thereon by heat or pressure rollers. In such instances, where the entire indicator body is porous and water absorbable, the lower surface 20 thereof may be rendered water impervious by adhering, laminating or sealing thereto a layer 30 of moisture-proof foil, plastic of other material, as shown by way of example, in FIG. 2.

Whether the indicator body 12 is made of pulp-impregnated filter paper or plastic foam, it is preferred that the body 12 be sufficiently flexible so that the indicator strip 10 may be made in a very long length and wound upon a supply spool for feeding the indicator body strip continuously to the apparatus which applies the stripes 22, 24, 26 and 28 in accordance with the manufacturing process to be presently described. An indicator body 12 made of a foam plastic is easily made sufficiently thin to afford such flexibility, without sacrificing the required structural strength.

The stripes 22, 24, 26 and 28 are applied to the porous upper surface 19 of the indicator body 12 in spaced lines which run parallel to the longitudinal edges 14, 16 of the body 12. The structure of the indicator body makes possible the application of the stripes by printing or coating directly on the upper surface of the indicator body utilizing the techniques and apparatus well known in the printing or coating fields.

One of the stripes, for example the stripe 22 constitutes a comparison stripe and contains only a nutrition substrate, for example a substrate consisting of broth, gelatine, agar or the like, which is selected as a suitable culture medium for growth of the suspected microorganism to be tested. Each of the other stripes 24, 26 and 28 consists of a mixture of this same nutrition substrate with a different bactericidal or bacteristatic drug which is known to destroy or retard the growth of the particular microorganism being tested.

The invention herein contemplates a method of manufacture of the indicator 10 by imprinting the stripes 22, 24, 26 and 28 simultaneously and continuously in a mass production operation utilizing relief printing machines, rotogravure printing machines, or the like since these methods, developed over generations in other fields, are especially suited to the mass production operation of coating a length of carrier material with a printed film of predetermined depth. Where paper or a porous plastic foam which is absorbent is used as the constituent material of the indicator strip, the strip is capable of absorbing or retaining the substrate, drugs and any necessary supplementary substances to whatever volume is required. If there is a need to apply drugs to the carrier material in a relatively thick layer, a rapid and uniform application of the drugs as thick stripes may be achieved by following the processes and utilizing the automatic equipment conventionally employed in the industrial application of glues or other viscous coatings to planar surfaces.

The application of the stripes to the upper surface of the indicator body 12 by printing or coating machines may be performed in a sterile environment to prevent undesirable pre-contamination of the indicator. In such an environment, a long length of the indicator body strip 12 is supported in wound-up condition on a supply spool or spindle and fed through the printing or coating apparatus for application of the stripes, from which the length of strip may either be wound on a take-up reel or cut into transverse panels of suitable size and packaged while still in sterile condition.

The separated indicators, which may be single panels 34, or a series of joined panels, are individually packaged in sealed containers while still in the sterile room or enclosure within which the printing process is performed. This aseptic method of manufacture has the advantage of insuring the sterility of the applicator and avoiding the necessity for subsequent sterilization of the indicator just before its use for testing, which sterilization process might well effect the reliability of the indicator. The containers in which the indicators are packaged may be sealed plastic envelopes, for example, or may simply be two sheets of film sealed along their edges. In any event, it is preferable that the container be of the type which is easily opened and which can be reclosed. Thus, where a section of joined panels is packaged, the container can be opened by the physician who separates and uses a single panel and replaces and reseals the remaining section for later use.

Figure 3:
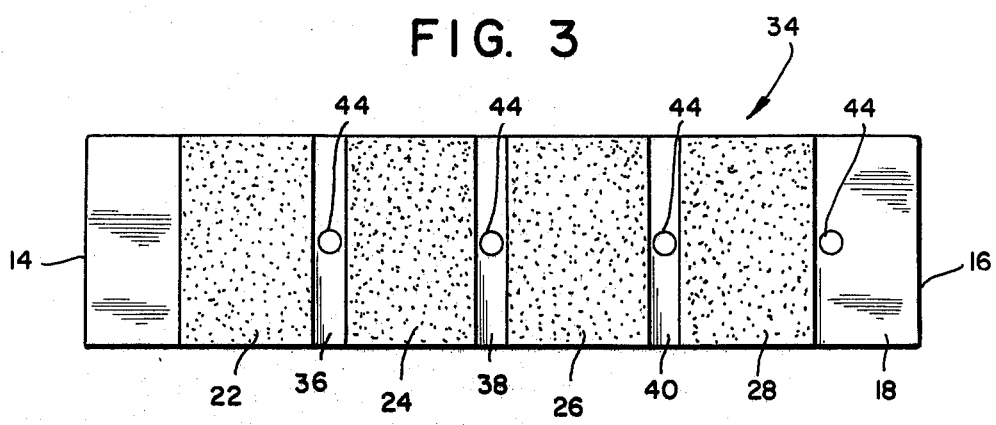
FIG. 3 is a top plan view, on an enlarged scale, of an indicator panel cut transversely from the strip of FIG. 1 and ready for use.

As shown in FIG. 1, the strip body 12 may be formed with separation grooves 32 extending transversely across the body 12, that is in a direction perpendicular to the stripes 22, 24, 26 and 28, and evenly spaced along the length of the strip body 12. Particularly where the strip body 12 is made of foam plastic, these separation grooves 32 may be employed to permit the strip body 12 to be easily divided into small transverse panels, each containing segments of the entire series of stripes 22, 24, 26 and 28, thereon. FIG. 3 illustrates a transverse panel 34 formed by separating the elongated indicator 10 of FIG. 1 along adjacent score lines 32. In manufacture, the printed or coated elongated indicator strip 10 may be separated into individual transverse panels 34 along each of the separation grooves and the panels 34 then individually sealed in sterile packages for subsequent distribution. Alternatively, the elongated indicator 10 may be cut apart in sections at each sixth, tenth or twelfth separation groove 32, for example, in order to produce a strip section containing a reasonably small number of panels 34 interconnected by the respective separation grooves 32. These strip sections may be individually packaged and supplied to physicians, who, after opening the package, may separate the sections into individual panels simply by tearing or breaking them apart at the separation grooves just prior to using them for testing.

In use of the applicator 10 for testing, the physician would normally saturate the porous upper surface of a single panel 34, or a small group of connected panels, with a specimen taken from the patient and containing the selected microorganism. A smear of the specimen may be easily applied across the surface of the panel 34 by means of a swab or the like, taking care that the smear makes even contact with all of the stripes 22, 24, 26 and 28, and after a suitable period, cultivation results may be observed. By examining the growth of the microorganism colony along the comparison stripe 22 which contains only the nutrient substrate, and comparing the growths or lack of growth along the other stripes 24, 26 and 28, the physician can visually determine which of the drugs contained in the latter stripes is the most effective for treating the patient infected by the tested strain of microorganism.

It will be observed in FIGS. 1 and 3 that the stripes 22, 24, 26 and 28 are spaced apart from each other and separated by respective linear bands or stripes 36, 38 and 40. An important feature of the invention herein is the manner in which the areas of the porous upper layer of the indicator body in the vicinity of these bands 36, 38 and 40 are made into moisture barriers to prevent migration of the coated drugs from one stripe to another. Since the indicator body 12 is made of a material which is heat sensitive or pressure sensitive, or both, during the processing of the indicator by the printing methods, as described above, the moisture barriers may be applied by the application of heat and/or pressure to the indicator body during such processing. Thus, where the indicator body 12 is fed through a machine for the printing of the testing stripes 22, 24, 26 and 28 thereon by rollers, for example, the same machinery may incorporate pressure rollers, heated rollers or heated pressure rollers for providing moisture barriers in the bands 36, 38 and 40 between the stripes. The formation of these moisture barriers may be done simultaneously with the application of the printed testing stripes on the indicator body, or in a separate run. In either event, effective moisture barriers are formed in an economical, mass produced manner without the necessity for adding additional barrier-forming materials to the indicator.

Where the indicator body 12 is made of foam plastic such as polyurethane foam having open cells, the application thereto along the linear bands 36, 38 and 40, of rollers or discs which are heated and/or under pressure, will cause the open cells therebeneath to close and become moisture-tight. Thus, an effective migration barrier is formed along the entire extent of said bands to insure that the coated drugs will not migrate between the stripes 22, 24, 26 and 28, even where the indicator body 12 is made fully or partly porous or penetratable. In this manner, the readily soluble bactericidal or bacteristatic drugs are prevented from leaking out to areas outside of their original placement, and a most precise visual analysis of the reactions on the indicator can be made.

Where the indicator body 12 is made of a porous paper with its pulp impregnated with a heat sensitive and/or pressure sensitive binder such as plastic or a resin, the application of heat and/or pressure by rollers in the manner described above, will cause the pulp fibres to compress or adhere, forming moisture barriers in the applied areas.

Figure 2:
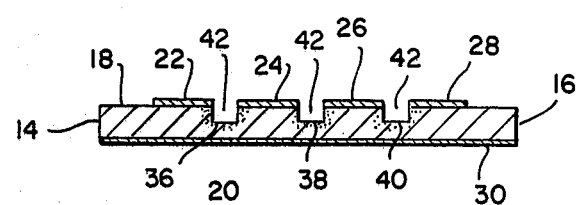
FIG. 2 is an enlarged section taken along line 2—2 of FIG. 1.

The barrier-forming rollers are preferably shaped to make depressions in the indicator body 12, as indicated in FIGS. 1 and 3. FIG. 2 shows, for example, a shallow rectangular groove 42 in each of the separation bands 36, 38 and 40. These grooves 42 may be made as deep as is practical, avoiding undue structural weakening, and may optionally be made in a variety of other configurations, such as with V-shaped, U-shaped cross-sections. The depressions 42 are made by the heated or pressure rollers or discs, and the indicator body in the vicinity of the depressions is compressed or fused to provide the migration barrier. It will be appreciated that, advantageously, the migration barriers need be formed only on the front, porous surface of the indicator body 12, since migration the opposite rear side is prevented by the moisture-tight backing thereon.

In a similar manner, to prevent migration or creeping of the drugs from one panel 34 to another, when said panels in joined condition are employed for simultaneous testing, the separation grooves 32 may be made wide and in the V-shaped form shown in FIG. 1.

It is desirable to identify the drug or substrate content of each of the stripes by imprinting a coded symbol, color spot, drug name or other indicia on the surface of the indicator 10 adjacent to or upon each of the stripes 24, 26, and 28. FIG. 1 shows, by way of example, a plurality of color coded symbols 44 printed on the upper surface of the indicator body 12 adjacent the respective stripes 22, 24, 26 and 28, with each symbol 44 being of a different selected color in order to identify the content of its associated stripe. Some of these symbols 44 are printed on the barrier bands 36, 38 and 40. As a practical matter, since the indicator body 12 is provided with a smooth water-impermeable lower surface 20, this lower surface is particularly adapted to receive this printed matter, and the symbols 44 may be printed on this lower surface beneath the associated stripe on the upper surface 18. The color coded symbols or other identification markings may be printed by the same machines and at the same time that the stripes 22, 24, 26 and 28 are imprinted on the indicators, so that the identification markings are applied in a fool-proof manner without the possibility of marking the stripes incorrectly. In addition, the lower surface of the indicator provides a ready and convenient location for the printing of instructions in the use of the applicator, or other informational material.

In the drawings, the indicator 10 is shown, by way of illustration, as having four spaced stripes 22, 24, 26 and 28. It will be appreciated, however, that the indicator may be made of such width as to receive a greater number of stripes. For the testing of certain microorganisms, it would not be unusual to imprint twelve or more stripes, each containing a different antibiotic or drug. In addition, it is to be understood that the indicator may be manufactured in the form of a wide sheet rather than the relatively narrow strip shown in FIG. 1. These sheets may be imprinted, in one printing operation, with a plurality of spaced groups of stripes, and, after imprinting, the sheets may be severed or otherwise divided between these groups of stripes to produce a plurality of elongated testing strips of the type shown in FIG. 1.

The manufacturing process of the invention will be further appreciated by reference to the following examples:

EXAMPLE 1

In a closed sterile room preferably with transparent walls or windows, a supply reel or spindle is mounted. On the reel or spindle is wound a roll or carrier material made, for example, of sterilized filter paper in which the pulp has been impregnated with a plastic or resin at the paper mill, and which is provided with a water-impervious backing. Alternatively, the carrier material may be a layer of plastic foam having open cells at its front surface, and on its rear surface either closed cells or a backing of liquid impermeable paper or plastic film.

In the sterile atmosphere the roll of carrier material in unwound, and during such unwinding the front of the carrier material is covered with a number of bactericidal or bacteristatic drugs in the form of spaced-apart longitudinally-extending stripes by coating methods well known in the printing and graphics industry, industrial application of glues and the like. In the linear bands or spaces separating the stripes sealed longitudinally-extending migration barriers are applied by heated or pressure rollers or discs.

When the applied drugs have dried, the length of carrier is imprinted at short intervals with identification signs on or adjacent to each stripe of drug, either on the front or the rear surface of the carrier, and transverse separation lines are impressed to permit the carrier to be divided into individual test strips. While still in the closed room, the coated and imprinted length of carrier material is then led through a cutting machine which cuts up the length into sections, the cuts being applied transversely to the longitudinal axis of the length of carrier material, and each severed section is individually inserted into a sterile re-closable container, and the latter is then sealed. The filled containers are then led through a sterile lock to a machine which packages the containers in larger boxes or other containers for hospital use or for wholesale distribution.

EXAMPLE 2

The fabrication of the indicators is performed in the same manner as described in Example 1, but in this instance the carrier strips are fabricated by the dozens in the form of sheets with spaced sets or groups of drug and culture stripes printed thereon, and with separation grooves or perforations located between the respective sets.

The full sheet is vacuum packed in a sterile container comprising an envelope or two sheets sealed together at their edges, and the front covering film of the container, or both the front and rear covering films are provided with weakened or separation lines registering with the separation grooves on the indicator sheet. After distribution in this form, the user can separate the packed sheet as desired into individual indicator strips, without removing the remainder of the sheet from the package.

While preferred embodiments of the invention have been shown and described herein, it is obvious that numerous additions, changes and omissions may be made in such embodiments without departing from the spirit and scope of the invention.

What is claimed is:

1. An indicator for use in the selection of bactericidal and bacteristatic drugs, comprising a solid elongated carrier sheet having an upper layer with a porous front surface and a moisture-tight backing, said upper layer being made of heat or pressure sensitive material that has interconnected passages pervious to moisture and being of a material consistency that permits said passages to be closed solely by application of heat or pressure without application of any additional moisture-sealing material, a plurality of testing coatings arranged on said front surface in spaced relationship to each other, said testing coatings comprising a plurality of spaced stripes on said porous front surface and extending parallel to the longitudinal axis of said carrier sheet, one of said coating stripes consisting only of a nutrition substrate for bacteria and constituting a comparison stripe, the other coating stripes constituting a mixture of a nutrition substrate and a different bactericidal or bacteristatic drug, and a moisture barrier band consisting of said passages that have been closed between each adjacent pair of said coating stripes formed by the application of heat or pressure to the front surface of said carrier sheet, said carrier sheet comprising a continuous length of adsorbent or absorbent sheet material with said porous front surface serving as an integral mechanical carrier for said testing coatings, said carrier sheet being adapted to be separated transversely at even intervals into small transverse panels, each containing said coating stripes, the coating stripe sections on said panels, when impregnated by a testing specimen, serving as individual bacteria culture media, whereby differences in bacteria colonization between the comparison stripe and the other coating stripes may be ascertained by direct visual observation.

2. An indicator according to claim 1 which also includes a plurality of evenly spaced separation lines extending transversely of said carrier sheet and perpendicular to said coating stripes, for separation of said sheet.

3. An indicator according to claim 1 in which said carrier is a thin layer of plastic foam.

4. An indicator according to claim 1 in which said carrier is a strip or sheet of paper having pulp impregnated with a resin.

5. An indicator according to claim 2 in which said separation lines comprise transverse grooves formed in the foam plastic body of said carrier.

6. An indicator according to claim 3 in which said plastic foam has open cells on its front surface and closed cells on its rear surface. With said rear surface being planar and capable of receiving printed matter thereon.

7. A method for the fabrication of an indicator for use in the selection of bactericidal and bacteristatic drugs, said method comprising the steps of introducing into a sterile environment a sterilized length of a sheet-like carrier made of a porous material having interconnected passages capable of becoming moisture sealing when exposed solely to heat or pressure, applying to a porous surface of said carrier a plurality of spaced coatings in the form of parallel stripes extending longitudinally along the length of said carrier and separated by porous linear bands, one of said coatings consisting of a nutrition substrate for bacteria and the other coatings consisting of a mixture of said nutrition substrate with respective different bactericidal or bacteristatic drugs, applying heat or pressure to said porous bands between said spaced stripes in an amount sufficient to close the interconnected passages of said porous material so as to provide moisture barriers between said stripes, and packaging at least a portion of said carrier in a sealed container prior to removing it from said sterile environment.

8. A method according to claim 7 which includes the additional step of cutting the coated carrier into transverse strips along cut lines extending perpendicularly to said longitudinal stripes, said packaging step comprising the insertion of said transverse strips into sterile re-closable containers.

9. A method according to claim 7 in which said longitudinal stripes containing said nutrition substrate and drugs are applied to the carrier surface by printing.

10. A method according to claim 7 in which said moisture barriers are applied by heated rollers.

11. A method according to claim 8 in which said moisture barriers are applied by pressure rollers.

12. A method according to claim 7 which includes the additional step of providing on said sheet-like carrier a plurality of evenly-spaced separation lines extending transversely thereof and perpendicularly to said longitudinal stripes before insertion of said carrier into said sealed container.

* * * * *